United States Patent [19]

Newman

[11] Patent Number: 5,668,634
[45] Date of Patent: Sep. 16, 1997

[54] QUALITY CONTROL AND GRADING SYSTEM FOR MEAT

[76] Inventor: Paul Bernard David Newman, Northcote House, Northlew, Okehampton EX20 3BT, England

[21] Appl. No.: 362,439

[22] PCT Filed: Jul. 5, 1993

[86] PCT No.: PCT/GB93/01398

§ 371 Date: Mar. 1, 1995

§ 102(e) Date: Mar. 1, 1995

[87] PCT Pub. No.: WO94/00997

PCT Pub. Date: Jan. 20, 1994

[30] Foreign Application Priority Data

Jul. 3, 1992 [GB] United Kingdom ............. 9214188
Oct. 7, 1992 [GB] United Kingdom ............. 9221065
Mar. 23, 1993 [GB] United Kingdom ............. 9306046

[51] Int. Cl.[6] ............................................. A22B 5/00
[52] U.S. Cl. ............................... 356/445; 348/89; 452/157
[58] Field of Search ......................... 356/445; 348/89, 348/92; 452/157

[56] References Cited

U.S. PATENT DOCUMENTS

| | | | |
|---|---|---|---|
| 3,154,625 | 10/1964 | Kail | 356/445 |
| 4,226,540 | 10/1980 | Barten et al. | 356/445 |
| 4,413,279 | 11/1983 | Gorl | 356/445 |
| 4,939,574 | 7/1990 | Petersen et al. | 356/445 |
| 5,194,036 | 3/1993 | Chevailer et al. | 452/198 |

*Primary Examiner*—Richard A. Rosenberger
*Attorney, Agent, or Firm*—Larson and Taylor

[57] ABSTRACT

Automated grading of meat (carcasses or cuts, particularly pork legs) employs the steps of: a) obtaining a representative image, or representative images, of a meat cut; e.g. using video cameras; b) processing said representative image or representative images to provide data relatable to the fatness of said meat cut; c) processing data provided at step (b), so as to produce one or more parameters suitable for categorizing the meat cut and/or the carcass from which the meat cut was taken; suitable parameters include the amount of fat or lean tissue, the location of fat tissue and the predicted yield of meat product; and d) comparing said parameter(s) with values stored in a database to determine the overall grading of said carcass or meat cut.

5 Claims, 4 Drawing Sheets

QUALITY CONTROL AND GRADING SYSTEM FOR MEAT

TECHNICAL FIELD

This invention relates to the control and assurance of the quality of meat (which may be in the form of carcasses or cuts of meat), and a grading system for the same.

Most meat processors wish to pay the producer of a meat animal according to the value they gain from each carcass, most obviously with regard to the amount of lean tissue derived therefrom. Despite the self-evident desirability of such an arrangement it is in fact surprisingly difficult to achieve practically with any degree of accuracy or satisfactory reproducibility.

BACKGROUND ART

A plethora of carcass grading systems and techniques have been developed which attempt to relate carcass characteristics to yield; most are performed manually and are therefore inherently subject to variations. With the intention of eliminating operator variability, I have previously devised an automatic inspection system using video cameras and image analysis; the system is disclosed in GB2247524 which is incorporated herein by reference. The system provides information on specific sex, distribution and other attributes through examination of the total carcass so as to determine an overall grade: weighting factors, such as carcass weight and size, may be applied if thought desirable. Normalised measurements are used to predict meat yield by reference to data from prior measurement of reference carcasses; as the database on which prediction of meat yield expands, the precision and accuracy of prediction steadily improves. Examination of the carcass can provide at best only a crude estimate of the quality of the meat itself.

One of the main causes of variability in the quality of meat and meat products is the variability of the meat cuts from which the meat is derived or which provide the raw material for the process concerned. Many of the causes of this variability have been identified, at least in broad sweep, but in practical terms the control of the causes that lead to such variability is extremely difficult. This is particularly the case from the point of view of the producer of meat animals, who is frequently faced with a highly variable and poorly defined genotypic pool, on which has to be superimposed a wide variety of environmental factors which contribute to the rate that the animal grows and the deposition of the relative proportions of the various tissues that make up the animal at slaughter. Further, the complex interplay between genotype and environment is only partly understood and inadequately defined. Consequently, both the fresh meat handler and the manufacturer of meat products are likely to be faced with the problem of unpredictably variable raw material for the foreseeable future.

In some respects, the great diversity of meat products that are available in the market today has originated in response to the variability in raw material characteristics, with particular types of cut tending to be used for product manufacture (because their appearance is not aesthetically attractive visually, for example, or their high content of connective tissue makes them unacceptably tough, etc) and the need to maximise return from individual cuts that are not of sufficient quality to be sold without processing. Despite the long history of meat processing, it is still common practice for manufacturers of meat products to select meat cuts according to criteria largely based on experience on one hand, and customers' requirements on the other. Where, as in many cases, this selection is largely manual and frequently subjective, it is typically somewhat slow, requires skill and experience on the part of the selector, and in practice is found to provide an unacceptably high incidence of unsatisfactory product. Where the selection is made on more objective criteria, such as weight, it may be less error prone; however, variability in the finished product is still too high, probably because the relationship between the objective value measured and the quality criterion in the end product is poor. These problems are further complicated and exaggerated in the large-scale manufacture of meat products, where throughput has to be high enough to handle the meat from several thousand animals a day, and allocate the individual cuts of meat to a particular product line at the same time. The vagaries of supply of raw material, and the need to be able to respond rapidly to a change in customers' requirements, places an increasing requirement for flexibility in manufacture.

The situation is a general and familiar one relating to all cuts of meats from all meat species, and is well exemplified in the processing of pig legs to hams. At one extreme of the spectrum of products that may be manufactured from a pork leg is the traditional ham, which is often sold as an intact, bone-in joint which may have taken weeks or even months between the time of excision from the pig carcass to the sale and consumption of the end product. At the other end of the spectrum, there are the products of the latter-day technologies such as tumbling and massaging, in which boneless pieces of meat are mechanically agitated and recombined during cooking; these products may be ready for sale within a few days of excision. The price per unit mass of the finished product commanded by the traditional ham is frequently considerably greater than that of the modern ham.

A quality parameter that is considered essential in most meat processing plants is the weight of end product sold related to the weight of raw material used in the process concerned. In the manufacture of hams from uncured pork legs, this weight is usually expressed as a yield, defined as the weight of end product expressed as a percentage of the weight of the pork leg. It is important that the yield is predictable within as closely defined limits as possible, in order to meet customers' specifications, and frequently also legislation. For this reason, yield is always a major criterion in any meat manufacturing plant, and it is often the only quality criterion used regularly in small meat processing plants. Similar considerations apply in connection with the meat carcass from which the cuts have originated.

The accurate prediction of weight of end product obtainable from an individual cut of meat is an ideal which has been sought throughout the meat industry for decades. The fatness of a meat cut may be a factor contributing to the variability in yield of cuts of meat, but the relationship is not well defined.

The term "fatness" relates not just to the total amount of fat in a cut, but also its distribution. A cause of complaint in the manufacture of traditional, bone-in ham is attributable to the variability in the magnitude of appearance of popliteal fat, which appears between blocks of muscle at the distal part of the leg behind the knee joint. The appearance of this fat depot has lead to its common name "star" fat. Excessive star fat is only seen in a traditional ham when it is sliced at the point of sale. Since conventional methods of quality control have failed to predict the predisposition of individual pigs to exhibit objectionable amounts of star fat, the complaint occurs at the point of sale to the domestic customer. Such complaints cause dissatisfaction (and incur expense) at all links in the chain between the product manufacturer and the consumer.

The occurrence of excessive star fat is not only unsightly, it also causes problems in the slicing of hams off the bone. Slices of ham containing large amounts of star fat between the muscle blocks tend to fall apart during and after slicing, leading to an unacceptably high incidence of rejected slices. If it were possible to identify before manufacture those pork legs most likely to exhibit unsatisfactory amounts of star fat, then these legs could, for example, be re-routed for the manufacture of lower value, boneless hams, when the popliteal fat could be removed by butchery.

Pig loins are less well-suited to tumbling or massaging, but the removal of subcutaneous fat from around the eye muscle is inherently simpler manually. The amount of fat trimmed may vary, for example removing as much of the fat as possible to leave a high-lean cut, or trimming less severely to provide a loin in which the eye muscle has an even fat thickness along its entire length. The resultant cut may be bone-in or boneless. Trimming of this sort may be undertaken as a routine matter (for example where the larger cross-sectional area of a more mature animal is considered advantageous but the associated fat is considered detrimental) or in cases where the amount of fat present over the eye muscle varies from animal to animal, in which case the trimming is intended to bring individual cuts within specification. In either case, the fat removed will typically be used for further manufacture, usually for comminuted meat products. Loins may be trimmed in this fashion to provide otherwise unprocessed cuts of high lean content, or the trimmed lean may be cured, smoked, etc.

Although trimming loins is inherently simple, it is also inherently slow when done manually (at least to achieve a high degree of evenness of trim without damaging the eye muscle), especially since a barrier to the increase in speed that may be achieved manually is an associated increase in risk of injury to the operatives. Loin pulling machines are available which attempt to overcome these difficulties. In essence, these consist of U-shaped flexible knives the design of which has evolved from similar implements used manually. Although mechanised, such apparatus still requires human control and supervision. In practice, the quality of trim achievable with these machines is not high, and in many cutting plants a secondary trimming is often performed manually.

The colour of meat and products is important. Products or cuts that are paler or darker than the normal expected for a particular cut or type of product are usually less desirable to the consumer.

Another cause of complaint is variability in colour. Where such variability is present in a pig leg, the leg can in principle be routed for boneless ham manufacture where, for example, muscles from a large number of pig legs may be selected on the basis of colour such that variability in colour in the end product is reduced to a minimum. Selection "by eye" is, of course, applicable in this situation, but it is found to be surprisingly unreliable, perhaps due to poor and variable lighting conditions typical in meat cutting and manufacturing plants, and is inherently too slow to keep pace with the necessary throughput demanded by the large scale manufacture of meat products.

There is rather less flexibility where pig loins show colour variability, since the eye muscle is less suited to tumbling or massaging. Where flaws in such colouration occur in this cut it usually results in down-grading, or possibly routing to a different product line, for example where the cut receives some heat treatment which can reduce some types of variability in colour.

A common type of flaw in colour in loins is dark areas against a paler background, although instances occur of loins exhibiting both pale and dark areas against a more normal meat colour. Other colour variability flaws include "blood splash" and bruising, although neither type of flaw is unique to loins.

One aspect of variability in colour of loin muscle which may be considered desirable by some markets is the presence or absence of visible fat within the loin muscle. This characteristic, termed "marbling", is believed to be linked to good eating quality in pork and beef. Excessive marbling, however, may be downgraded on its appearance; thus, intramuscular fatness is another example where the distribution of fat, rather than just its absolute amount, is linked to quality and grading.

When the quality of a particular cut of meat influences the type of product made from that cut, as is the case with most of the forgoing examples, it usually also affects the financial value of the cut. Such alteration in the value of a cut must also change the net return on the carcass from which the cut originated. Existing carcass grading systems cannot easily accomodate value fluctuations of this type which only arise after grading, once breakdown of the carcass not primals has begun; since grading should ideally reflect the overall value of the carcass, this fact highlights an inherent weakness of these systems.

DISCLOSURE OF INVENTION

Surprisingly, I have found that data relatable to the fatness of a meat cut are also relatable to the total lean content of the carcass from which the meat cut was taken to such a degree that satisfactory grading of the carcass can be achieved by this relationship. This is especially so when the cut is porcine ham when these data may be used to provide a carcass grading system which incorporates a more accurate estimate of the lean content of the economically important ham than existing systems. Carcass weights would normally be included as data in such a system, as would the weight of the cut itself. The accuracy of estimation of the total lean content of a carcass from these data, with or without the inclusion of data on carcass weight, is further enhanced by inclusion of data on carcass conformation, which may be obtained manually or through the use of apparatus such as that described in GB2247524.

The present invention provides in one aspect a method of grading carcasses comprising
  a) obtaining a representative image, or representative images, of a meat cut;
  b) processing said representative image or representative images to provide data relatable to the fatness of said meat cut;
  c) processing data provided at step (b), optionally in association with data obtained from the carcass from which the meat cut was taken, so as to produce a parameter or plurality of parameters suitable for categorising the carcass from which the meat cut was taken; and
  d) comparing said parameter or plurality of parameters with values stored in a database to determine the overall grading of said carcass.

The data obtained from the carcass from which said meat cut was taken which may be associated and processed with the data of step (c) are preferably either carcass weight or conformation, or both, and are most preferably carcass weight and a plurality of dimensions obtained by the steps of checking for the presence of the carcass in the field of view of a camera, exposing an image of the carcass from a plurality of different viewpoints, and determining said plurality of dimensions of said carcass from said images.

Another aspect of the present invention provides in one aspect a method for the grading of meat cuts for subsequent processing to produce a meat product, comprising (a) obtaining a representative image, or representative images, of said meat cut;

(b) processing said representative image or representative images to provide data relatable to the fatness of said meat cut;

(c) processing data provided at step b) so as to produce a parameter or plurality of parameters suitable for categorising said meat cut; and (d) routing said meat cut to a grade or category on the basis of said parameter or plurality of parameters.

In many circumstances, the method includes the additional and optional step of determining the weight of the meat cut and including said weight as data to be processed in step (c). Weight may be determined directly or indirectly. The representative image obtained at (a) is preferably an image of an area of exposed meat obtained using a video camera. Step and the optional step of determining the weight of the meat cut may be undertaken sequentially in either order, or they may be undertaken concurrently.

Preferably a parameter produced at step (c) is the total amount of lean tissue in the meat cut; conversely, a said parameter may be the amount of fat, or the location of that fat, or both. Preferably a parameter produced at step (c) is the predicted yield of meat product. Optionally, when the meat cut is a hind leg from a pig, a paramater produced at step (c) is the predisposition to the occurrence of higher than a predetermined acceptable level of popliteal fat. Optionally, the method also includes obtaining data on the colour of the cut of meat and using said data to provide another said parameter. Optionally, the method comprises an additional step of obtaining data on the variability in colour of the cut.

A further aspect of the present invention provides a method for the grading of meat cuts for subsequent processing to produce a meat product, the method including the additional step of trimming the meat cut (the term "trimming" being taken to mean the removal of tissue, especially adipose tissue, from the meat cut), the trimming step being controlled by a suitably programmed processor using the data produced at step (b), and/or the parameter or plurality of parameters produced from those data in step (c). The additional step of trimming may be considered as either preceding step (d) (in which case it is the trimmed cut that is routed to a grade or category); or it may follow step (d), in which case the trimming is of the graded or categorised cut. It will be appreciated that the grade assigned to a cut of meat may have a certain level of trimming associated with that grade.

In yet another aspect of the present invention, there is provided a method for grading a hind leg of a meat animal according to the amount of popliteal fat, comprising (a) obtaining a representative image, or representative images, of a hind leg of a meat animal;

(b) processing said representative image or representative images to provide data relatable to the amount of popliteal fat present in said hind leg;

(c) processing data produced at step (b) so as to produce a parameter or plurality of parameters suitable for categorising said hind leg; and (d) routing said hind leg to a grade or category on the basis of said parameter or plurality of parameters.

According to a further aspect of the present invention, there is provided equipment for carrying out the methods of the invention.

In some situations the grade assigned to a cut may not involve further processing (other than chilling, freezing or cooking); that is, the cut is deemed suitable for sale as a conventional meat cut, either fresh, frozen or cooked.

MODES FOR CARRYING OU THE INVENTION

Figure 1:
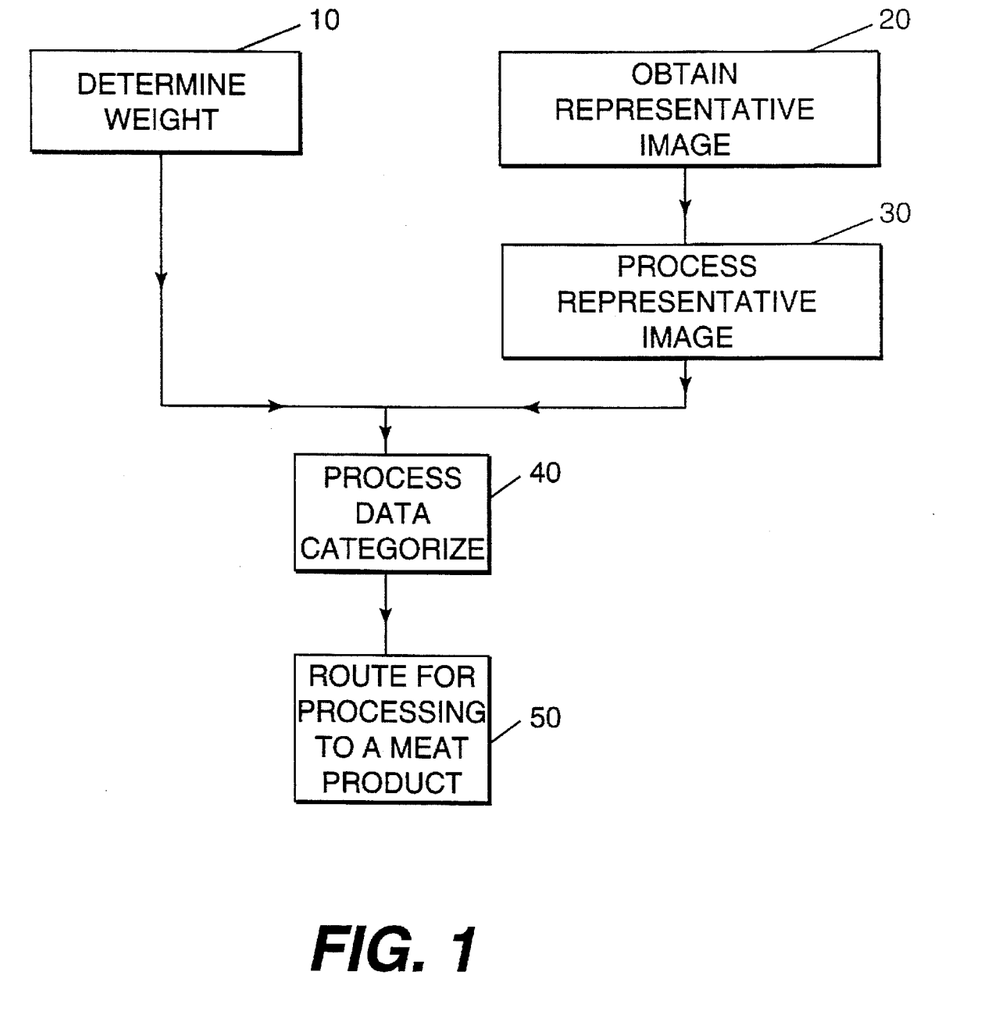
FIG. 1 is a block diagram depicting steps of the invention as applied to grading meat cuts.

Referring firstly to FIG. 1; at its simplest, suitable equipment for carrying out the method of the present invention usually comprises means for determining the weight of the cut 10; means for obtaining a representative image of the cut 20; means for processing said representative image of the cut 30; a data processing unit 40 for processing the weight and image data so as to provide a parameter or plurality of parameters suitable for categorising said cut, and which stores a standard value or standard values of the parameter or plurality of parameters and uses these to assign the cut to a pre-defined category; and an effector or router 50 which receives instructions from the data processing unit 40 dependent upon the category to which the cut has been allocated, and acts upon those instructions to route the meat cut for processing according to the decided category.

EXAMPLE 1

Figure 2A:
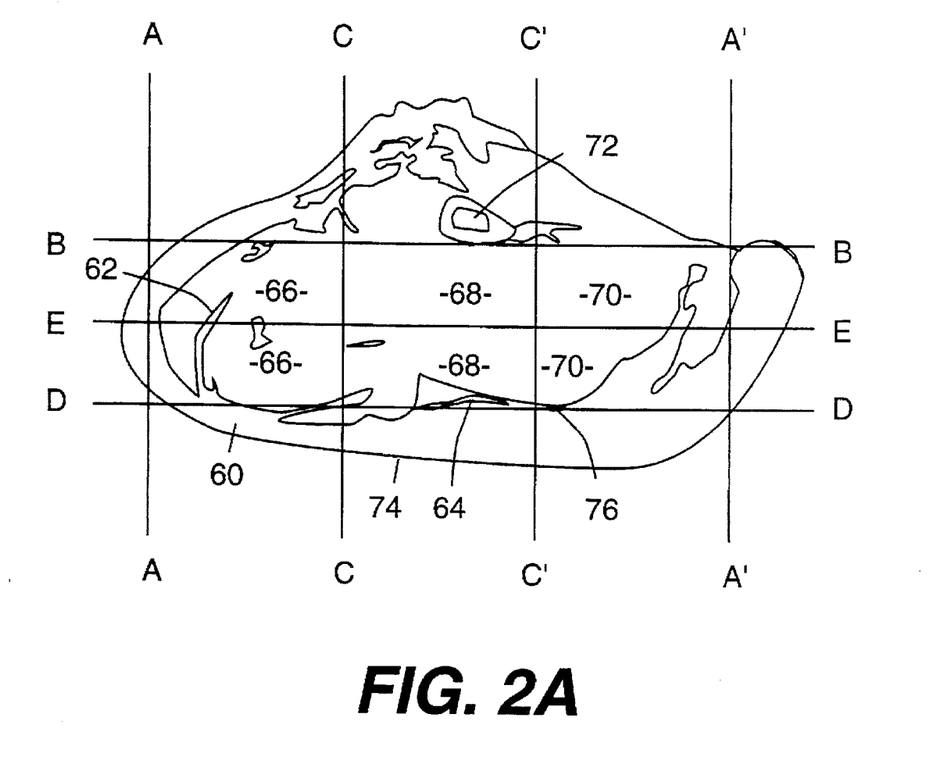
FIG. 2a is a representative image of a leg of pork, on which are displayed the areas from which data relatable to fatness are obtained in a preferred embodiment of the invention.
Figure 2B:
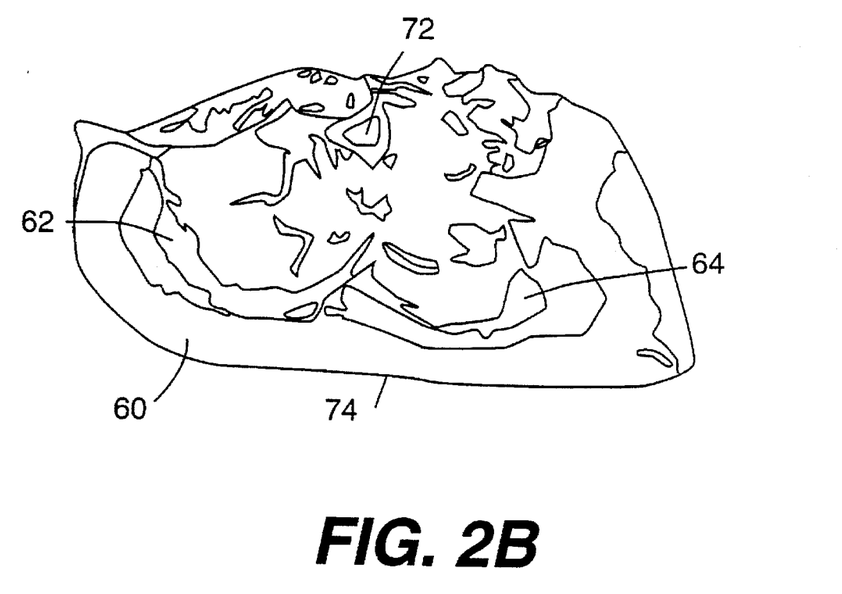
FIG. 2b illustrates an example of a similar leg of pork more disposed to a high level of star fat.

In an automated system embodying the method of this invention, a pork leg such as that shown in FIG. 2a or 2b is moved along a belt to a first station where the leg is weighed. The weight of the leg is sensed by suitable means and stored in a data processing unit. An initial selection based solely on weight routes only those legs within a predetermined range for processing into traditional hams.

If it is within the suitable weight range, the leg moves to a second station where an image of the exposed broad end of the leg is obtained by a video camera. The original image captured will include inconsequential background as well as the image of the pork leg. The first stage of image processing is therefore to provide a first window, defined by the outline of the cut without any background, as shown in FIG. 2. This is the representative image of the meat cut, within the original image. The total area of the exposed cut surface is determined from this image, and the maximum and minimum lengths of the exposed cut surface in two mutually perpendicular directions. This image may be further processed to determine the total lean area, based on the light reflective properties of the different tissues.

As also shown in FIG. 2, the data from the first image also serve to provide the image processor with information to set up a second window (defined by the lines A—A, & A'—A'). The mean thickness of the underside fat 60 within the second window is determined.

In some applications of the method, satisfactory categorisation can be obtained using the two criteria of weight and underside fat thickness. I have found, for example, that there is a very strong correlation between carcass weight, subcutaneous fat thickness at the cut surface of the excised limb (underside fatness), uncured leg weight and the final weight of the ham after curing and smoking.

In attempting to find a satisfactory and meaningful relationship between and within the data collated, a large number of components were correlated and regressed using a multi-variate analysis technique. Hypotheses were tested for significance using analysis of variance, F-ratio, t-test, chi-squared and Wilcox ranking as appropriate.

No (or very low) significance values were found with all combinations of uncured, green, cured and in/out smoke weights. There was no significant improvement with the introduction of carcass weight or Fat-0-Meter value. However, a correlation of r=0.86 was found between (log (carcass weight/underside fat thickness)) and (out of smoke weight/uncured excised leg weight).

As correlating uncured weight to out of smoke weight had already been established as non-significant this positive correlation suggested that both carcass weight and underside fat thickness were significant component influences on ultimate yield.

Table 1a shows the effect of correlating underside fatness with [out of smoke weight/uncured excised leg weight] at constant carcass weight. Table 1b shows the effect of correlating carcass weight with [out of smoke weight/uncured excised leg weight] at constant fatness. The correlations for 1a ranged from 0.91–0.96 and for 1b from 0.86–0.93.

The effects were highly significant. The different correlation values and in particular the different slopes also suggest that there is an additional non-linear effect between low and high fat thicknesses and between light and heavy carcass weights.

More data, particularly on carcass weight:fatness:yield variation, would, of course, make it possible to produce a curve fit equation that will further reduce the variability in prediction equations outlined in table 1c. However, the use of variable constants accounted for more variability in the prediction equations. These values ranged from 0.5 for predicted yields in excess of 80% of raw weight to 2.5 for those below 70%.

The equation accounted for much of the variation in the population and there was good correlation between actual and predicted ham yields.

TABLE 1a

CORRELATION OF UNDERSIDE SUBCUTANEOUS FAT THICKNESS TO YIELD AT CONSTANT CARCASS WEIGHT

| Fat Thickness (mm) | Yield $\frac{\text{out of smoke wt} \times 100}{\text{uncured leg wt}}$ | No. (n) | Correlation (r) |
|---|---|---|---|
| 11 | 82.14 | 6 | 0.96 |
| 24 | 74.32 | 8 | 0.93 |
| 36 | 68.11 | 5 | 0.91 |

Carcass Weight Range 161 lbs–165 lbs

TABLE 1b

CORRELATION OF CARCASS WEIGHT TO YIELD AT CONSTANT UNDERSIDE SUBCUTANEOUS FAT THICKNESS

| Carcass Weight (lbs) | Yield $\frac{\text{out of smoke wt} \times 100}{\text{uncured leg wt}}$ | No. (n) | Correlation (r) |
|---|---|---|---|
| 147 | 73.52 | 4 | 0.86 |
| 165 | 77.56 | 7 | 0.90 |
| 178 | 76.29 | 6 | 0.93 |
| 195 | 75.64 | 5 | 0.88 |

TABLE 1c

PREDICTION EQUATION TO ESTIMATE OUT OF SMOKE YIELD FROM FAT THICKNESS DETERMINED FROM A REPRESENTATIVE IMAGE AND WEIGHT OF LEG CUT $Y_1 = (Y = a - b(x)) + C$

Where
- $Y$ = Estimated Yield out of smoke (as % of raw weight)
- $Y_1$ = Modified Y value including compensating factor
- $a$ = Computed intercept value
- $b$ = Slope Constant
- $x$ = Actual fat thickness of sample
- $C$ = Compensating Factor $Y_1 = (Y = (92.5 - (0.8 * \text{Fat thickness})) + C$ $C$ = 0.5 if Y value is greater than 80%;
1.5 if Y value is greater than 69.9% but less than 80%;
2.5 if Y value is less than 69.9%.

Thus $Y_1 = Y + C$, and $Y = (a - bx)$.

Thus, where grading is effected solely on yield, adequate information on fatness can be obtained by determining from the representative video image the mean subcutaneous fat depth. (Alternatively, fat depth at predefined locations is a satisfactory indication of fatness). In this example, as shown in FIG. 3, pork legs with a predicted yield less than a predetermined minimum are routed for processing into commodity hams; legs having predicted yields above a predetermined value are routed for boneless ham manufacture.

In this trial, knowledge of carcass weight improved the accuracy of the prediction of yield, but it is not an essential pre-requisite for the method of the invention as categorisation could be achieved quite adequately without it.

In a further trial, I have found that underside fat thickness, total fat content and amount of intermuscular fat, all of which are determinable from the representative image, correlate well with the total amount of lean tissue present in the leg. This sort of information is extremely useful for assessing the amount of raw material available for the manufacture of boneless hams, for example.

Figure 3:
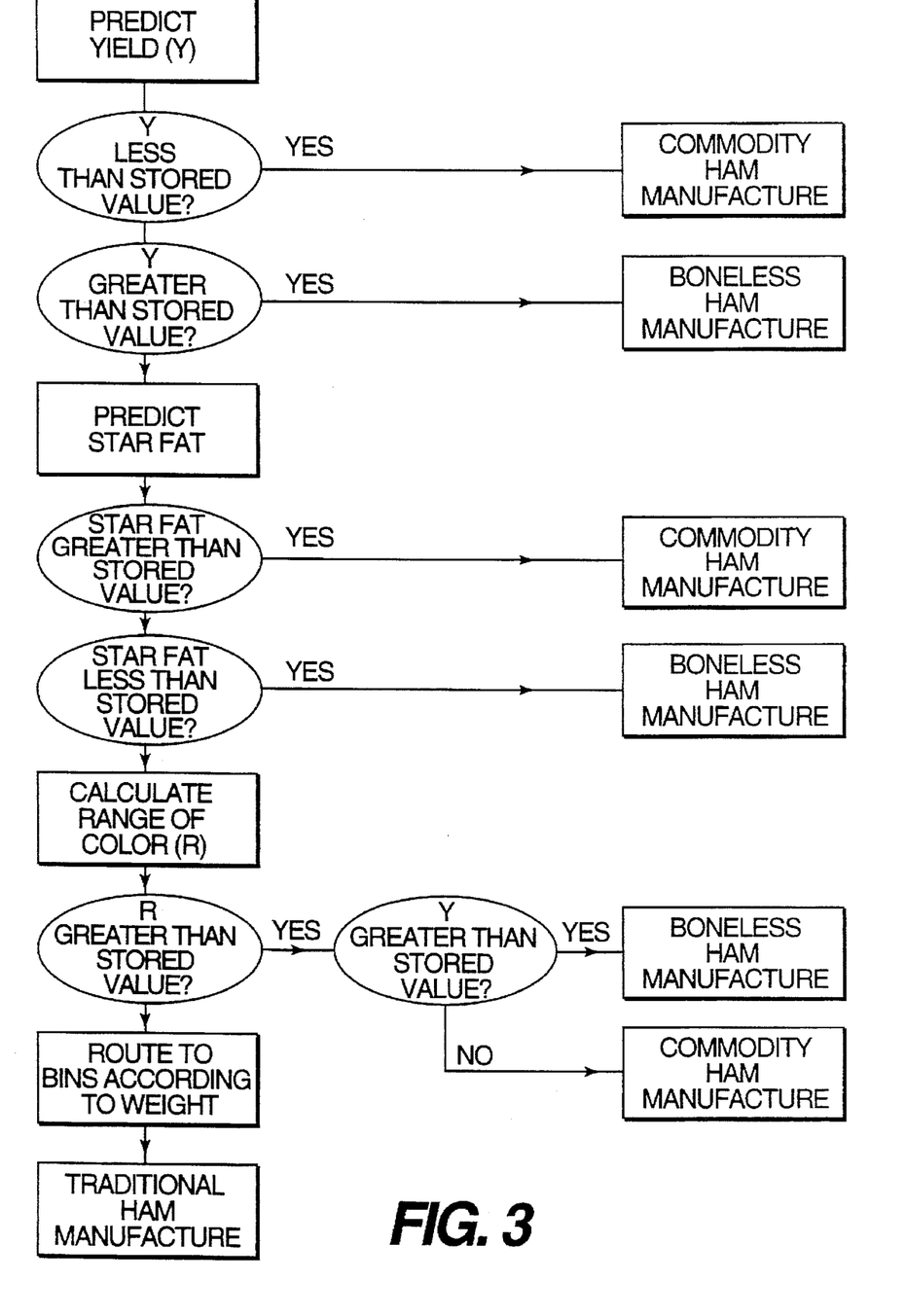
FIG. 3 is a flow diagram illustrating the use of various parameters to route pork legs for processing to hams in an illustrative example of the method of the present invention.

Further quality parameters, obtained from the representative image may be used for categorisation, as shown in FIG. 3. Another parameter suitable for categorising a pork leg is the predicted amount of star fat. The thickness of underside fat 60 is not a good predictor of the amount of star fat; however, I have found that the amount of intermuscular fat 62,64 present on the exposed surface does correlate well with the amount of star fat in the deeper leg. In a trial, over 90% of legs found to have an unacceptable amount of star fat had prominent intermuscular fat in these regions (as shown in FIG. 2b, for comparison with FIG. 2a), although differences in underside fat thickness were small.

The amount of intermuscular fat 62,64 in the region of interest may be estimated by defining three further windows 66,68,70 within the second window. The upper boundary of these windows (line B—B in FIG. 2a) is located immediately below the cut bone 72 and runs approximately parallel to the underside skin 74. The boundaries between windows 66,68,70 are defined by lines C—C, C'—C', respectively, which are perpendicular to line B-B and equidistant between lines A—A, A'—A'. The lower boundary of the windows (line D—D) is located by reference to the upper edge 76 of the underside fat layer 60.

Mean greyness values for each window 66,68,70 are suitable indicators of the amount of star fat. This method of analysis is suitable for most circumstances, but a more sensitive routine is to generate an additional window whose upper boundary is defined by line E—E. This line is located equidistant between lines B—B, D—D; line D—D is the lower boundary of the window. Within this window, connectivity analysis (which provides information on shape, size, area etc.) is undertaken, ignoring all structures that touch the boundaries of the region of interest. This procedure isolates the larger areas of intermuscular fat which are used to quantify the amount of the star fat. Legs having predicted star fat values greater than a stored upper limit are routed for processing to commodity hams, while legs having predicted star fat values lower than a stored lower limit are routed for boneless ham manufacture.

With the correct use of optical conditions, the representative image is able to convey information on colour. Under green illumination, the spectral response may be used as a colour parameter, the legs being categorised according to mean colour value or colour value at specific locations.

A parameter of colour variability can be obtained by calculating the maximum difference between the green spectral response obtained from windows 66,68,70, for example. In this example, and as shown in FIG. 3, legs having too great a range in spectral response are routed for boneless ham manufacture if their calculated yield is above a predetermined value, or they are routed for commodity ham manufacture if their predicted yield is below that value.

Pork legs routed for traditional ham, ie those within the pre-defined acceptable ranges for weight, fatness, star fat, and colour, are then routed to particular bins on the basis of weight.

Dedicated apparatus can, of course, be manufactured to effect the methods of this invention but without determining the weight of the meat cut. Such apparatus would be particularly suitable where, for example, yield is of less importance than ensuring that variability in colour is not excessive, or to avoid extremes of colour. Similarly, the ability to detect and remove from manufacture pig legs likely to display an unacceptable amount of star fat during slicing may be of greater importance to the manufacturer of traditional ham than yield.

With suitable modifications, and with reference to appropriate databases (usually derived empirically), a system for grading shoulders can be devised. A criterion suitable for grading shoulders is the total amount of lean tissue, with shoulders graded as having a comparatively large amount of lean tissue being routed for retail butchery; a further criterion to be satisfied for routing for retail butchery is likely to be evenness in colour. Shoulders graded as being unsuitable for retail butchery might be routed for boning out to provide either raw material for sale as minced pork, or raw material for sausage manufacture, categorisation to either grade being determined perhaps on the colour of the shoulder.

Similarly, suitable modifications may be made to the details in this example to provide a system suitable for grading loins, given the existence of an appropriate database. An example of such a system can be deduced from Example 2. A commercially important criterion that could be included in such a system could be the predicted shelf life of the cut, perhaps estimated by reference to a database relating colour as measured by the system to colour measured after a defined time under a defined set of conditions.

EXAMPLE 2

The following example illustrates the application of the invention to include the guidance of an automated trimming operation.

Figures 4, 5B:
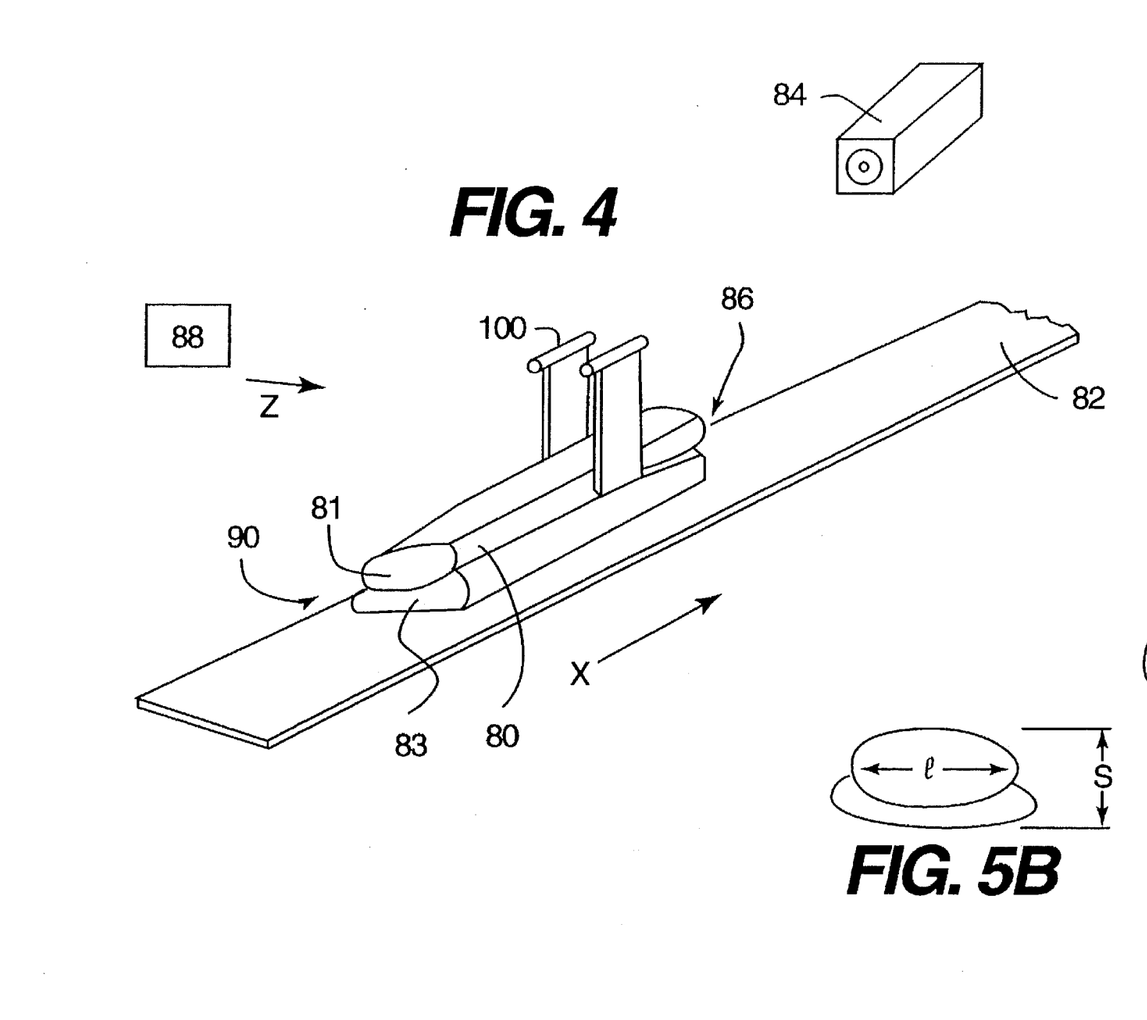
FIG. 4 shows an example of the invention in which pig loins are trimmed as part of the grading, the degree of trim being determined from, and guided by reference to the representative image.
Figure 5A:
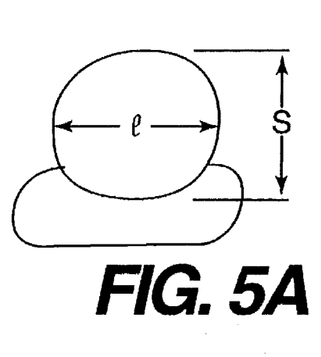
FIG. 5 shows examples of characteristics of shape of eye muscle which may be used to provide categorising criteria: 5(a), anterior face; 5(b) posterior face.

As illustrated in FIGS. 4 and 5, a loin of pork 80 is moved along a moving belt 82 in the direction shown by the arrow X. A video camera 84 obtains a representative image of the area of exposed meat at the foremost end 86 of the cut 80, in this case the anterior end of the loin. The representative image obtained by video camera 84, similar to that shown as FIG. 5(a), is processed to determine the total lean area (primarily the area of eye muscle m. longissimus dorsi 92), and the depth of the fat 94 associated with the lean. Using techniques similar to those discussed in Example 1, the data from the first image serve to provide the image processor with information to set-up a second window isolating the eye muscle 92. This second image may in turn be processed to provide a categorising criterion of colour, which is a particularly important quality criterion of loin lines. The image may also be processed to check for the presence of colour flaws. The second image may also, or alternatively, be processed to provide a categorising criterion based on the degree of marbling. In this example, categorisation is made primarily on the colour of the eye muscle and the presence or absence of colour flaws, the information on the amount of fat and lean present in the first image being used to control the amount of trimming given to cuts which satisfy the colour criteria.

Since the video camera 84 is in an elevated position relative to cut 80 and directed obliquely, it is also able to provide an accurate estimate of the length Y of cut 80. A second video camera (not shown, but positioned at 88 and directed so as to be able to obtain a representative image of the trailing end 90 of the loin 80 ) may be used to provide confirmatory information on length Y, and also obtain a representative image of the other end 90 of loin 80, such as that shown in FIG. 5b. An image of the eye muscle 96 may again be formed by the generation of a suitable window, and this image processed to provide criteria on colour and colour flaws. The assessment of colour of this image is compared with that obtained from the foremost end 86 to provide a criterion of colour variability along the loin.

FIGS. 5a and 5b illustrate the sorts of differences in shape seen at either end of the loin. The loin end shown in 5a has a somewhat circular shaped eye muscle 92 in association with a comparatively deep layer of subcutaneous fat 94. FIG. 5b shows an eye muscle 96 in association with subcutaneous fat 98, but in this case the eye muscle 96 has a greater amount of asymmetry, and the back fat 98 is less deep.

A meat cutter faced with the requirement to trim off excess back fat and presented with a surface such as that depicted in FIG. 5a is unable to guess the way in which the shape of eye muscle 81, and the relationship between the eye muscle 81 and the back fat 83 changes along the length Y of cut 80. This is especially the case when he is presented only with the foremost end 86 of the loin 80, as is invariably the case with non-automated on-line machinery of the prior art. However, accurate trimming can be obtained by directing the cutting of U-shaped knife 100 according to data on shape of foremost end 86 and other end 90, and length Y obtainable from the representative images captured by the first video camera 84 and the second video camera positioned at 88. The values obtained provide data which may be compared with data in a database of relative shape change along the loin possibly when used in association with information on the weight of the cut. A variety of parameters exist to define shape, and the suitability of any sub-set of parameters is assessed on a trial and error basis; satisfactory results have been obtained using absolute area of eye muscle (92, 96), the ratio [longest axis:shortest axis] of eye muscle (marked 'l' and 's' respectively in FIGS. 5 (a,b)), the ratio [area:length of perimeter], and other parameters suitable for assessing change in shape with constant area and change in area with constant shape.

The database may be obtained from trials in which individual loins are cut at various locations along their length, and determining the shape change along the loin, for example by dissection. The cutting action of U-shaped knife 100 is controlled by a suitably programmed computer. The extent of trimming will depend on the specification associated with the grade; for example, it may remove substantially all the subcutaneous fat ("supertrim") or alternatively leave a thin layer of fat along the entire length of the cut ("finetrim").

I claim:

1. A method for grading a hind leg of a meat animal according to the amount of popliteal fat, comprising:
    a) obtaining a representative image, or representative images, of an exposed surface of a hind leg of a meat animal;
    b) processing said representative image or representative images to determine the amount of intermuscular fat present at the exposed surface, thereby providing data relatable to the amount of popliteal fat present in said hind leg;
    c) processing data provided by step (b) so as to produce a parameter or plurality of parameters suitable for categorising said hind leg; and
    d) routing said hind leg to a grade or category on the basis of said parameter or plurality of parameters.

2. A method according to claim 1 in which, in step b, the amount of intermuscular fat is determined in a predefined region of the representative image or images.

3. A method according to claim 2 in which the amount of intermuscular fat is estimated by including in the processing of step b estimation of the mean greyness values of a plurality of predefined sub-regions within the predefined region of the representative image or images.

4. A method according to claim 3 in which the amount of intermuscular fat is estimated by including in the processing of step b connectivity analysis of a plurality of predefined sub-regions within the predefined region of the representative image or images.

5. Apparatus for grading hind legs of meat animals comprising conveying means for conveying a hind leg of a meat animal; at least one video camera positioned adjacent to said conveying means to obtain an image or images representative of an exposed surface of said hind leg; signal processing means to provide from said image or images data relatable to the amount of intramuscular fat present at the exposed surface thereby providing data relatable to the amount of popliteal fat present in the hind leg, and to produce from said data at least one parameter suitable for categorizing said hind leg; and means for routing said hind leg to a grade or category on the basis of said parameter.

* * * * *